(12) United States Patent
Kuo et al.

(10) Patent No.: US 8,851,071 B2
(45) Date of Patent: Oct. 7, 2014

(54) RESPIRATION HUMIDIFIER

(75) Inventors: Arthur Kuo, Lübeck (DE); Kai Brieger, Lübeck (DE); Tobias Otte, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1170 days.

(21) Appl. No.: 12/185,316

(22) Filed: Aug. 4, 2008

(65) Prior Publication Data

US 2009/0038614 A1 Feb. 12, 2009

(30) Foreign Application Priority Data

Aug. 8, 2007 (DE) .................. 10 2007 037 458

(51) Int. Cl.
*A61M 16/16* (2006.01)
*A61M 16/10* (2006.01)

(52) U.S. Cl.
CPC ........... *A61M 16/16* (2013.01); *A61M 16/109* (2014.02); *A61M 16/1075* (2013.01)
USPC .................................................. 128/203.26

(58) Field of Classification Search
USPC ............ 128/203.26, 203.27, 204.13, 200.11; 261/6, 70, 94, 104, 107, 120; 239/34; 62/315, 316
See application file for complete search history.

(56) References Cited

U.S. PATENT DOCUMENTS

| | | | | |
|---|---|---|---|---|
| 2,429,112 A | * | 10/1947 | Warren | 392/325 |
| 3,100,485 A | * | 8/1963 | Bartlett, Jr. | 128/201.13 |
| 3,355,155 A | * | 11/1967 | Heltzen et al. | 261/130 |
| 3,515,378 A | * | 6/1970 | Hill | 261/106 |
| 3,954,920 A | | 5/1976 | Heath | |
| 4,225,542 A | | 9/1980 | Wall et al. | |
| 5,399,299 A | * | 3/1995 | Stengel et al. | 261/30 |
| 6,575,436 B2 | * | 6/2003 | Litz | 261/27 |
| 6,755,396 B1 | * | 6/2004 | Weinrich | 261/30 |

FOREIGN PATENT DOCUMENTS

| | | |
|---|---|---|
| DE | 100 16 005 A1 | 12/2001 |
| DE | 601 21 083 T2 | 12/2006 |
| DE | 603 10 062 T2 | 6/2007 |
| EP | 1 138 341 B1 | 6/2006 |
| EP | 1 507 567 B1 | 11/2006 |

* cited by examiner

*Primary Examiner* — Tan-Uyen T Ho
*Assistant Examiner* — Peter S Vasat
(74) *Attorney, Agent, or Firm* — McGlew and Tuttle, P.C.

(57) ABSTRACT

A respiration humidifier (1), including a humidifying chamber (21), an inlet (10) for feeding breathing air (5) to be humidified into the humidifying chamber (21), an outlet (11) for releasing the humidified breathing air (9) from the humidifying chamber (21), a bottom (19) limiting the humidifying chamber (21) for receiving water (18) to be evaporated, water (4), which is received by the bottom (19) in the humidifying chamber (21) and is to be evaporated for humidifying the breathing air (5) and at least one distributor (2) with capillary and/or suction action, which is arranged in the humidifying chamber (21) such that this is in contact with the water (4) to take up water (4) in the distributor (2) and is in contact with the breathing air in the humidifying chamber (21) for evaporating the water (4) taken up on the surface of the distributor (2) into the breathing air (5). The respiration humidifier allows a high evaporating capacity to be reached with homogeneous air-vapor mixture at a low design effort. Furthermore, splash water is avoided in the humidifying chamber and the respiration humidifier is able to be manufactured at a low cost. This object is accomplished by the at least one distributor (2) covering at least 50% of the surface of the water (4).

12 Claims, 4 Drawing Sheets

RESPIRATION HUMIDIFIER

CROSS REFERENCE TO RELATED APPLICATIONS

This application claims the benefit of priority under 35 U.S.C. §119 of German Patent Application DE 10 2007 037 458.7 filed Aug. 8, 2007, the entire contents of which are incorporated herein by reference.

FIELD OF THE INVENTION

The present invention pertains to a respiration humidifier.

BACKGROUND OF THE INVENTION

The human nose acts as a means of actively heating and humidifying the breathing air under physiological conditions. However, the artificial respiration of patients requires that the nose be bypassed and the breathing air is sent directly into the human trachea with a tube (flexible tube). The inspired air must therefore be humidified and optionally also heated to physiological values in order to maintain the lung function in case of artificial respiration.

Prior-art respiration humidifiers have a humidifying chamber as a cavity with an inlet opening and with an outlet opening for the breathing air. Water to be evaporated is located at the bottom of the humidifying chamber. The vapor cannot disadvantageously be taken up completely by the breathing air because of the limited contact surface between the water and the air, on the one hand, and the high velocity of flow of the breathing air or the short residence time of the breathing air in the humidifying chamber, on the other hand, so that sufficient humidifying effect is not guaranteed. Furthermore, the necessary homogeneous mixing of the air and vapor is not possible in a satisfactory manner. In addition, the water may form a spray upon impact of the air jet from the inlet opening.

To reduce these drawbacks, provisions have already been made to insert in the humidifying chamber a guide body, which channels the flow of the breathing air in the humidifying chamber. The breathing air is guided here such that a direct impingement of the breathing air on the water is avoided and the breathing air is guided along a wall enclosing the humidifying chamber towards the water surface in order to obtain the necessary contact between the breathing air and the surface of the water. The relatively small cross-sectional areas of the breathing air channels formed by the guide body in the humidifying chamber lead to high flow velocities and hence to very short residence times, so that the uptake of vapor by the breathing air at the water surface is very limited.

To avoid splash water in the pipelines connected to the inlet opening and to the outlet opening, it is known that baffle plates can be arranged as a shielding against the splashing of water. These baffle plates cause a disadvantageous additional flow resistance for the breathing air and require an additional design effort and manufacturing cost.

U.S. Pat. No. 4,225,542 shows a class-forming respiration humidifier. The respiration humidifier has a ring-shaped cross section. The outer limitation of the humidifying chamber is formed by a water-absorbing material. The water present in the bottom of the humidifying chamber is in contact with the water-absorbing material, so that the water can rise up in the water-absorbing material. A tube, through which the breathing air to be humidified is introduced into the lower area of the humidifying chamber, is arranged concentrically in the interior of the humidifying chamber. The humidified air flows out again at the upper end of the humidifying chamber, so that the direction of flow of the breathing air in the humidifying chamber extends vertically from bottom to top.

Furthermore, a respiration humidifier of this class with a humidifying chamber of a rectangular cross section is known from U.S. Pat. No. 3,954,920. Water is present in the bottom of the humidifying chamber. The cover wall of the humidifying chamber has an inlet opening and an outlet opening for letting the breathing air in and out. Water-absorbing material is directed vertically in the humidifying chamber and dips into the water in the lower area, so that it can be taken up by the water-absorbing material for evaporation.

The vertical orientation of the water-absorbing material in the humidifying chamber in the upper area of the absorbing material disadvantageously brings about a low degree of saturation with water in both class-forming documents because the path over which the water must rise in this area is long. The absorbing material therefore has a high evaporation capacity in the lower area close to the water only. Furthermore, there is no protection against splashing of water caused by the breathing air flowing in, because only a small percentage of the surface of the water is covered by the absorbing material. The geometry of the absorbing material causes an unfavorable air flow, which fails to guarantee a reliable homogeneous mixing of the air and vapor.

SUMMARY OF THE INVENTION

The object of the present invention is therefore to make available a respiration humidifier, in which high evaporation capacity can be reached with a homogeneous air-vapor mixture at a low design effort. Furthermore, splash water shall be avoided in the humidifying chamber and the respiration humidifier shall be able to be manufactured at a low cost.

This object is accomplished with a respiration humidifier, comprising a humidifying chamber, an inlet means, e.g., an inlet opening or an inlet valve, for feeding breathing air to be humidified into the humidifying chamber, an outlet means, e.g., an outlet opening or an outlet valve, for releasing the humidified breathing air from the humidifying chamber, a bottom limiting the humidifying chamber for receiving water to be evaporated, water to be evaporated, which is taken up from the bottom in the humidifying chamber for humidifying the breathing air, and one or more distributors with capillary and/or suction action. The one or more distributors are arranged in the humidifying chamber such that the one or more distributors are in contact with the water for taking up water into the one or more distributors and is in contact with the breathing air in the humidifying chamber for evaporating the water taken up on the surface of the one or more distributors in the breathing air. The one or more distributors cover at least 50%, preferably at least 90% and especially 100% of the surface of the water. The one or more distributors includes a distributor structure made up of one or more composites.

The covering of the surface of the water with the distributor makes it possible for the breathing air flowing into the humidifying chamber not to cause any splash water. The sections of the water surface affected by the air flowing in are to be covered for this purpose with the distributor. Furthermore, the surface of the distributor has a larger evaporation surface compared to the surface of the water, so that the evaporation capacity of the respiration humidifier as a whole is increased. The covering of the surface of the water with the distributor is defined as both the direct covering of the surface of the water, i.e., the underside of the distributor is located in the water, and the indirect covering of the surface of the water, i.e., the underside of the distributor is located above the surface of the water. In case of indirect covering of the surface of the water with the distributor, the water is taken up into the distributor through a partial contact between the distributor and the water, e.g., through ribs.

In another embodiment, the maximum extension or the sum of the maximum extensions of the at least one distributor in the horizontal direction is greater than the maximum extension or the sum of the maximum extensions of the at least one distributor in the vertical direction. The small vertical extension of the distributor compared to the horizontal extension of the distributor causes the water to have to rise over a short section only, as a result of which there is a high degree of saturation of the distributor with water on the surface even in the upper area of the distributor, especially in the top-side protuberances, so that a high evaporation capacity can be reached on the entire surface of the distributor.

Protuberances, which are designed, e.g., as ribs or grids or as triangles or semicircles in diameter, are preferably provided on the top side of the at least one distributor. The protuberances enlarge the surface of the distributor, so that a larger surface is present for the evaporation of water. Furthermore, microvortices of water are formed between the protuberances, which improve the mixing of the air and water and increase the evaporation capacity due to the longer contact and residence time of the breathing air on the surface of the distributor.

In a supplementary embodiment, protuberances, which are designed as ribs or grids or as triangles or semicircles in diameter, are provided on the underside of the at least one distributor. The protuberances on the underside of the distributor increase the capillary suction capacity of the distributor, so that more water can be taken up by the distributor. The degree of humidity on the surface of the distributor and also the evaporation capacity of the distributor are thus increased.

The at least one distributor is preferably attached to a housing of the respiration humidifier, preferably in a detachable manner. The fixation of the position of the distributor causes that no water can enter the inlet and outlet opening and hence especially the tube (flexible tube) connected to the outlet opening in case of oblique position of the respiration humidifier if the surface of the water is completely covered by the distributor. The detachable fastening of the distributor, for example, by means of a snap-in or screw connection, makes it possible to replace the distributor in a simple manner and rapidly. In general, replacement of the distributor is necessary after a certain duration of use of the respiration humidifier, e.g., for hygienic reasons.

In particular, a partition, which supports or causes a circulating flow of the breathing air in the humidifying chamber, is present at the inlet and/or outlet means.

In an additional embodiment, the at least one distributor comprises, for example, cotton fabric, a textile fabric, a high-performance absorbent mat or a porous material.

In particular, the water and/or the distributor can be heated up by means of a heater. The heater can raise the water to higher temperatures, e.g., 60° C., in order to increase the evaporating capacity and hence the relative humidity of the humidified breathing air. In addition, the temperature of the humidified breathing air flowing out of the outlet opening can thus be controlled.

The heater is preferably integrated in the at least one distributor. Integration of the heater in the distributor makes it possible to raise the temperature predominantly into the range especially relevant for the evaporation capacity, namely, the surface of the distributor. A higher evaporation capacity can thus be reached with a relatively low energy consumption. Furthermore, the response time for increasing or lowering the relative humidity of the air and/or the temperature of the humidified breathing air is reduced.

In another embodiment, the heater has essentially a two-dimensional shape. It is designed, e.g., as a flat or curved surface and/or is provided with holes, slots or rectangles. The heater integrated within the distributor has, in general, a flat, plate-like geometry. In partial areas, e.g., in protuberances, which are designed as semicircles in the cross section, it may be necessary to design the integrated heater as a curved heater. The openings are necessary for the water to be able to flow unhindered, especially in the vertical direction, through the distributor to the surface of the distributor. The heater integrated in the distributor is preferably arranged centrally between the top side and the underside of the distributor.

However, the heater may also be arranged outside the respiration humidifier. In a preferred embodiment, a bottom limiting the respiration humidifier is made of metal, over which the heat is sent into the humidifying chamber.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
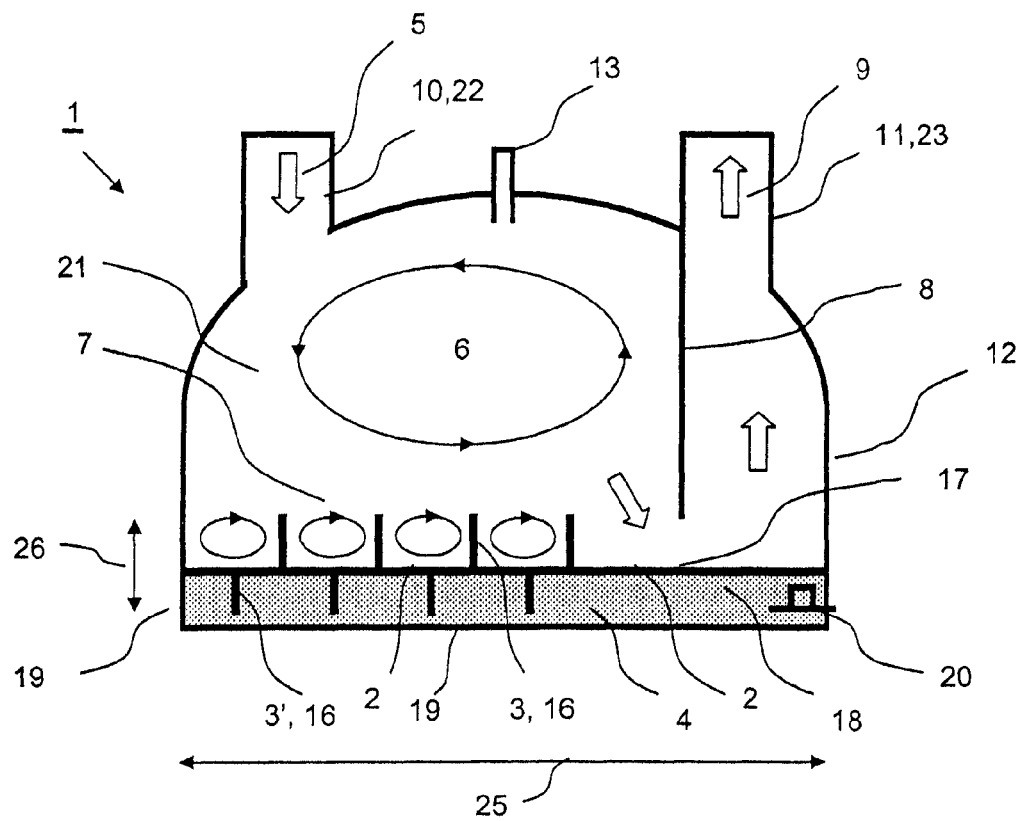
FIG. 1 is a schematic view of a vertical section of a respiration humidifier.
Figure 2:
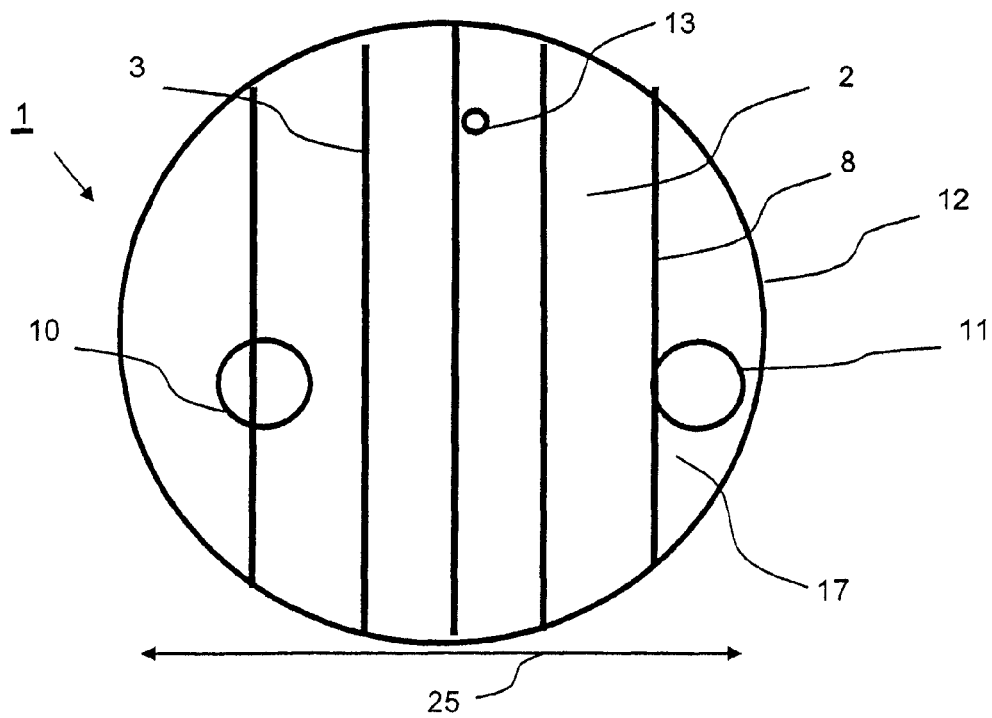
FIG. 2 is a schematic top view of a distributor with capillary and/or suction action according to FIG. 1.

Referring to the drawings in particular, FIG. 1 shows a schematic vertical section of a respiration humidifier 1 for humidifying and heating breathing air 5 to be humidified for the artificial respiration of patients. A humidifying chamber 21 is enclosed by a housing 12. The top side of the housing 12 is provided with an inlet means 10 designed as an inlet opening 22 for introducing breathing air 5 to be humidified into the humidifying chamber 21 and with an outlet means 11 designed as an outlet opening 23 for drawing off humidified breathing air 9 from the humidifying chamber 21. The breathing air 5 to be humidified flows through the inlet opening 22 into the humidifying chamber 21 and is again discharged as humidified breathing air 9 from the humidifying chamber 21 after taking up moisture or water vapor. In addition, a water inlet opening 13 for introducing water 4 into the humidifying chamber 21 is present. The housing 12 forms on the underside of the humidifying chamber 21 a water-proof bottom 19 for holding the water 4 to be evaporated. The top side or surface of the water 4 is completely covered by the disk- or plate-shaped distributor 2 with capillary and/or suction action. The diameter of the distributor 2 is 105 mm, which corresponds to a standard size. The maximum extension 25 of the distributor 2 thus equals 105 mm in the horizontal direction (FIGS. 1 and 2). Furthermore, FIG. 1 shows the maximum vertical extension 26 of the distributor 2 with respective ribs 3 and 3' designed at right angles to the disk- or plate-shaped distributor 2. The distributor 2 is in contact on the surface 17 with the breathing air 5 to be humidified in the humidifying chamber 21 and on the underside 18 with the water 4. The thickness of the distributor 2, i.e., the distance between the top side 17 and the underside 18, is in a range of 1 to 2 mm. The distributor 2 is preferably arranged in the humidifying chamber 21 such that a surface of the water 4 is located between the top side 17 and the underside 18 of the distributor 2. Splashing of the water 4 on entry into the breathing air 5 to be humidified through the inlet opening 22 of the inlet means 10 of the humidifying chamber 21 is effectively prevented from occurring with this arrangement of the distributor 2. Due to its capillary and/or suction action, the distributor 2 takes up the water 4 and drives it to the top side 17 of the distributor 2. The water 4 drawn up by the distributor 2 can evaporate on the top side 17 of the distributor 2, which is in contact with the breathing air 5 to be humidified, and it can thus humidify the breathing air 5 to be humidified. The evaporation of the water 4 subsequently takes place indirectly by means of the distributor 2 with capillary action (FIGS. 1 and 2).

The top side 17 of the distributor 2 is provided with protuberances 16 designed as top-side ribs 3. The top-side ribs 3 with a height of 10 mm enlarge the evaporating surface of the distributor 2 in order to obtain a higher evaporation capacity of the respiration humidifier 1. The distances between the individual ribs 3 equal 15 mm. In addition, the ribs 3 extend at right angles to the horizontal component of the direction of flow of the circulation 6 in the humidifying chamber 21 (FIG. 1), so that microvortices 7 are formed between the ribs 3. The microvortices 7 prolong the residence time of the air, improve the mixing of the air-vapor mixture and increase the evaporating capacity per unit area of the evaporating surface of the distributor 2 (FIG. 1).

The underside 18 of the distributor 2 with capillary action is provided with protuberances 16 designed as underside ribs 3'. The underside ribs 3' enlarge the surface of the distributor 2 wetted with water 4 and increase the capacity of the distributor 2 to take up water 4 and the water saturation on the top side 17 of the distributor 2. The underside ribs 3' prevent the water 4 from sloshing to and fro, as this happens, e.g., during the transportation of the respiration humidifier 1. The entry of water through the outlet opening 23 of the outlet means 11 and hence into the flexible breathing tube can be effectively prevented from occurring with the respiration humidifier 1 according to the present invention. The ribs 3' are preferably arranged at spaced locations from the bottom 19 of the humidifying chamber 21 (FIG. 1). This arrangement guarantees uniform distribution of the water 4 between the chambers formed by the ribs 3'. In another embodiment, the ribs 3' are in contact with the bottom 19 of the humidifying chamber 21, the ribs having recesses each in the area of the bottom 19, through which the water 4 can be distributed between the chambers formed by the ribs 3' (not shown). This embodiment guarantees high stability of the distributor 2 in the humidifying chamber 21. The maximum extension 26 of distributor 2 in the vertical direction corresponds to the distance between the ends of the top-side ribs 3 and the underside ribs 3' (FIG. 1).

Figure 3:
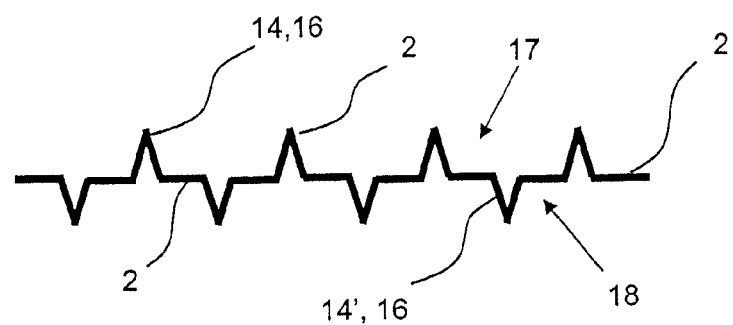
FIG. 3 is a schematic view of a vertical section of a second embodiment of the distributor.
Figure 4:
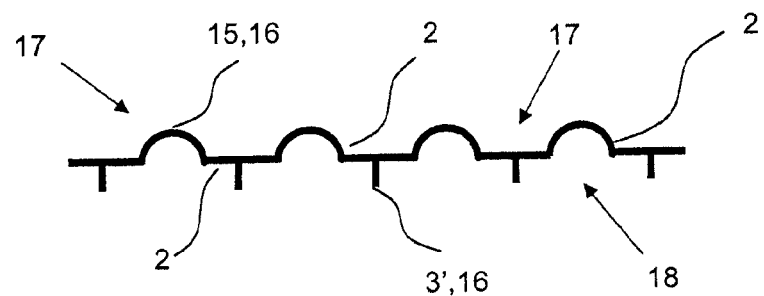
FIG. 4 is a schematic view of a vertical section of a third embodiment of the distributor.
Figure 5:
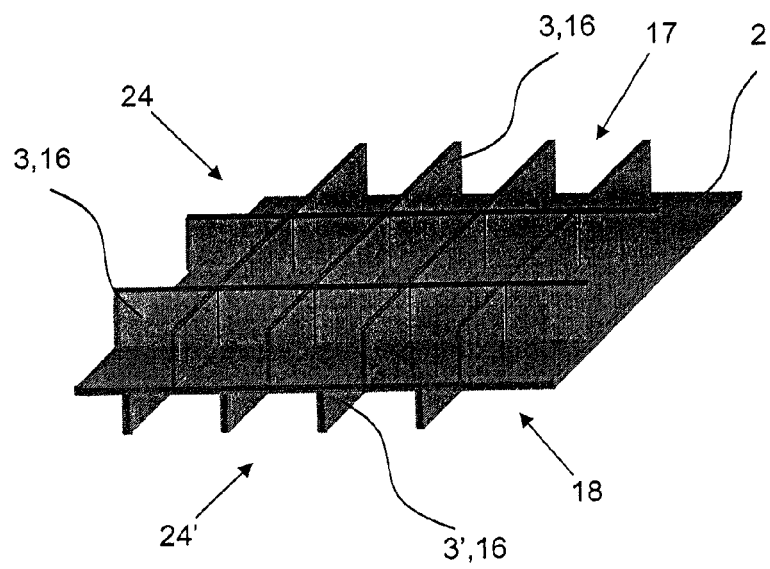
FIG. 5 is a perspective view of a fourth embodiment of the distributor.

The protuberances 16 of the distributor 2 may also be designed as triangles 14 (FIG. 3), as semicircles 15 and ribs 3' (FIG. 4) and as ribs 3, 3' in cross section, which are arranged in a rectangular grid 24 (FIG. 5).

A partition 8 at the outlet opening 23 extends into the vicinity of the distributor 2 in order to prevent the humidified breathing air 9 from being discharged prematurely from the outlet opening 23, so that a high relative humidity of the humidified breathing air 9 is attained. Furthermore, the direction of flow of the breathing air 5, 9 in the humidifying chamber 21, which is predetermined by the partition 8, supports the formation of a circulating flow 6. The circulating flow 6 leads to a homogeneous air-vapor mixture and increases the evaporating capacity, especially also due to the formation of the microvortices 7 (FIG. 1).

An electric heater 20 is arranged in the water 4 for heating the water 4 to be evaporated and the distributor 2 with capillary and/or suction action to a certain temperature, e.g., 60° C. (FIG. 1). To control the temperature of the water 4, a temperature sensor (not shown) is preferably provided in the humidifying chamber 21.

Figure 6:
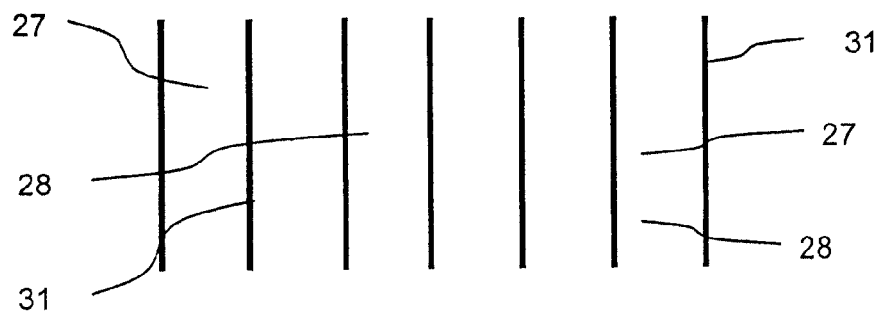
FIG. 6 is a top view of a first embodiment of a heater integrated within the distributor.
Figure 7:
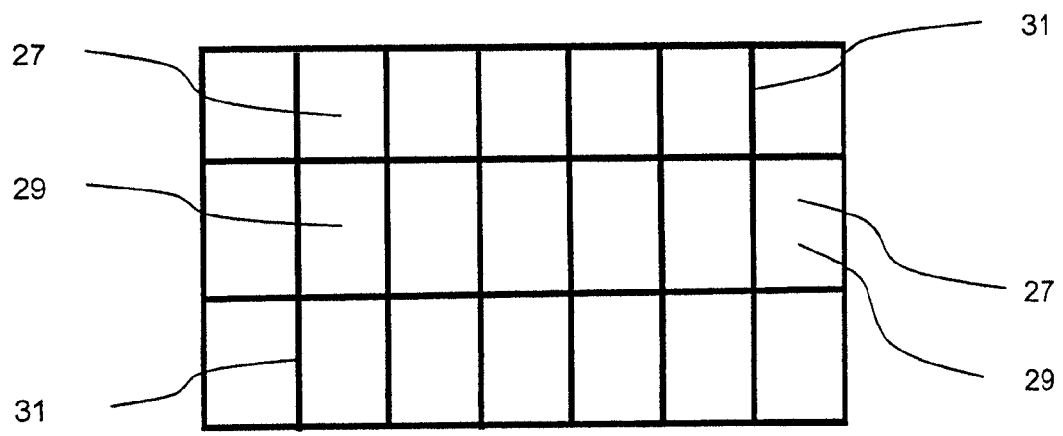
FIG. 7 is a top view of the heater integrated in the distributor in a second embodiment.
Figure 8:
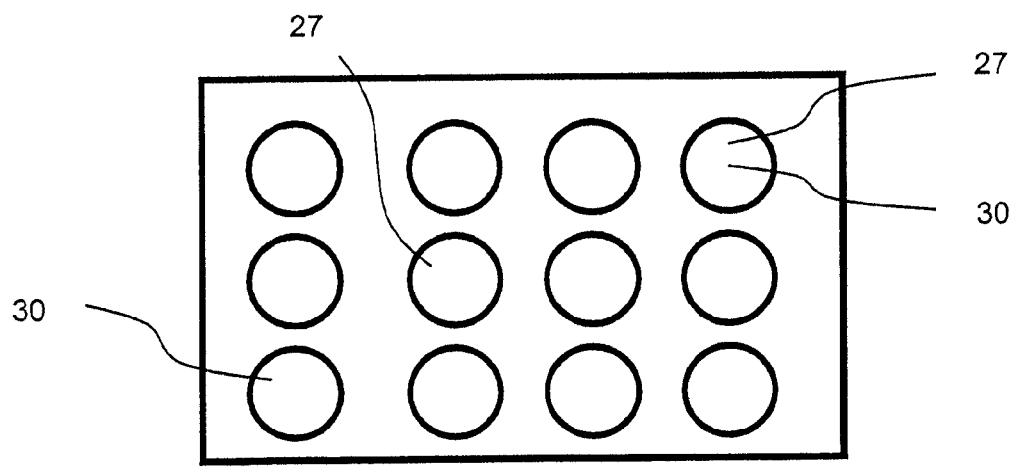
FIG. 8 is a top view of a heater integrated in the distributor in a third embodiment.

The heater 20 may also be integrated within the distributor 2 and is located centrally between the top side 17 and the underside 18 of the distributor 2 (not shown). In addition, the heater 20 integrated within the distributor 2 may also be arranged analogously in the protuberances 16. The heater 20 integrated within the distributor 2 has a two-dimensional shape and has openings 27 at right angles to the plane of the heater 20 integrated within the distributor 2 to ensure that water 4 can flow unhindered through the distributor 2 in all directions, especially in the vertical direction. The heater 20 integrated within the distributor 2 may comprise parallel heating wires 31, which have openings 27 as slots 28 (FIG. 6). The heating wires 31 may also be arranged in a grid-shaped pattern, so that the openings 27 are rectangles 29 (FIG. 7). Furthermore, a plate-like heater 20 may be provided with holes 30 (FIG. 8).

In another embodiment, the bottom 19 may be made of a metal, so that heat can be sent from a heater arranged in the respiration humidifier 1 into the humidifying chamber 21 (not shown).

The temperature of the water 4 or of the distributor 2 as a manipulated variable makes it possible to control the relative humidity of the air and/or the temperature, e.g., 37° C., of the humidified breathing air 9. A higher temperature of the water or of the distributor 2 brings about a higher evaporating capacity and a higher temperature of the humidified breathing air 9. Furthermore, temperature and/or humidity sensors and/or flow measuring means may be positioned at the inlet opening 22 and/or outlet opening 23 (not shown). Temperature and/or humidity sensors are preferably also provided on or in the distributor 2. The measured data of these sensors as well as of the sensor arranged in the water 4 are processed by a control unit and are used to control and/or regulate the temperature and the relative humidity of the humidified breathing air 9, especially by means of the temperature of the water 4 and/or of the distributor 2 (not shown).

The distributor 2 is fixed detachably in the housing 12, so that the water 4 cannot enter the inlet opening 22 and the outlet opening 23 in case the respiration humidifier 1 is in an oblique position. In addition, the air jet is advantageously prevented as a result from causing splashing of water 4. The distributor 2 can be easily replaced because of the detachable fixation.

The distributor 2 consists of an absorbent material, e.g., cotton fabric, a textile fabric or high-performance mat, or a porous material. The use of readily biodegradable organic materials for the distributor 2 has the advantage that the distributor 2 can be easily disposed of after use, e.g., by means of composting.

On the whole, considerable improvements are possible with the respiration humidifier 1 according to the present invention at a low design effort, i.e., at a low cost. The evaporating capacity is increased and thorough, reliable mixing of the humidified breathing air 9 and vapor is achieved. Furthermore, splash water formed by the breathing air 5 flowing into the humidifying chamber 21 is avoided, so that no water 4 can enter the outlet opening 23 and the tube (flexible tube) connected thereto.

Figure 9:
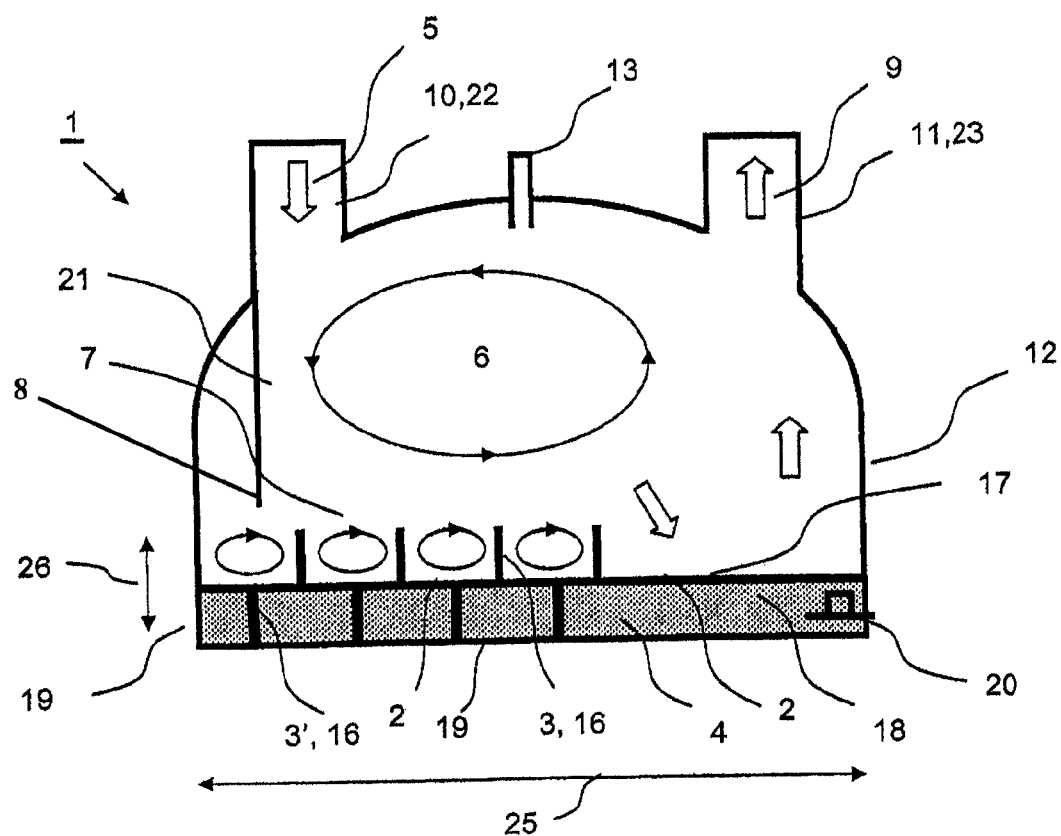
FIG. 9 is another schematic view a vertical section of another embodiment of a respiration humidifier.

FIG. 9 is a schematic view of a vertical section of another embodiment of a respiration humidifier. The partition 8 is located at the inlet means 10. The ribs 3' are in contact with the bottom 19 of the respiration humidifier 1.

While specific embodiments of the invention have been shown and described in detail to illustrate the application of the principles of the invention, it will be understood that the invention may be embodied otherwise without departing from such principles.

What is claimed is:

1. A respiration humidifier, comprising:
a respiration humidifier housing having a bottom respiration humidifier surface, said respiration humidifier housing defining a humidifying chamber, said respiration humidifier housing having an inlet and an outlet, said inlet receiving breathing air such that the breathing air enters said humidifying chamber, said respiration humidifier housing containing water partially filling said humidifying chamber to form a single unitary and contiguous humidifying chamber water surface, said water being in contact with said bottom respiration humidifier surface;
a distributor structure arranged in said humidifying chamber and fixed detachably in said respiration humidifier housing, said distributor structure having a first side in contact with the water such that said distributor structure absorbs water via capillary action or suction, said distributor structure having a second side in contact with the breathing air in said humidifying chamber such said water absorbed via said distributor structure evaporates into said breathing air to form humidified breathing air, said outlet receiving said humidified breathing air for delivery to a patient, said distributor structure extending along a surface of the water, wherein:
said distributor structure is an integral unitary capillary or suction distributor structure covering all of the water surface;
said first side of said distributor structure includes integral first side projections extending into said water in a direction away from the water surface, said first side projections being in contact with said water such that said first side projections absorb water via capillary action, said second side of said distributor structure having integral second side projections extending in a direction away from the water surface into a breathing air stream of breathing air that has entered said humidifying chamber, each second side projection being located at a spaced location from an adjacent second side projection to form a plurality of microvortice sections, said breathing air circulating within said microvortice sections to form said humidified breathing air.

2. A respiration humidifier in accordance with claim 1, wherein said first side projections and second side projections comprise ribs or said grids that are arranged at spaced locations from said bottom respiration humidifier surface of said humidifying chamber.

3. A respiration humidifier in accordance with claim 1, wherein said first side projections comprise ribs or said grids that are in contact with said bottom respiration humidifier surface of said humidifying chamber.

4. A respiration humidifier in accordance with claim 3, wherein said ribs or said grids define a plurality of recesses in an area of said bottom, said water being distributed through said plurality of recesses.

5. A respiration humidifier in accordance with claim 1, wherein said distributor structure comprises cotton fabric, a textile fabric, a high-performance absorbent mat or a porous material.

6. A respiration humidifier in accordance with claim 1, wherein said water and/or said distributor structure are heated via a heater.

7. A respiration humidifier in accordance with claim 6, wherein said heater is integrated within said distributor structure.

8. A respiration humidifier in accordance with claim 6, wherein said heater has a substantially two-dimensional shape, said heater comprising a flat or curved surface.

9. A respiration humidifier in accordance with claim 6, wherein said heater has openings, said openings comprising circular holes, slots or rectangular holes.

10. A respiration humidifier in accordance with claim 1, wherein said bottom respiration humidifier surface limiting said humidifying chamber is made of a metal.

11. A respiration humidifier in accordance with claim 1, further comprising a partition element located at one of said inlet and said outlet, said breathing air being delivered into said humidifying chamber via said inlet such that said partition element causes a circulating flow of said breathing air in said humidifying chamber, said respiration humidifier housing defining a water inlet opening for receiving water.

12. A respiration humidifier in accordance with claim 1, wherein:
said second side projections comprise ribs or grids or triangles in a vertical section of said distributor structure or semicircles in said vertical section of said distributor.

* * * * *